US010184858B2

(12) United States Patent
Klein et al.

(10) Patent No.: US 10,184,858 B2
(45) Date of Patent: Jan. 22, 2019

(54) VISUALLY INSPECTING OPTICAL FIBERS

(71) Applicant: COMMSCOPE CONNECTIVITY BELGIUM BVBA, Kessel-Lo (BE)

(72) Inventors: Marvin Klein, Rheine (DE); Milan Maksimovic, Deventer (NL); Gerard Cornelis Van Den Eijkel, Losser (NL)

(73) Assignee: CommScope Connectivity Belgium BVBA (BE)

( * ) Notice: Subject to any disclaimer, the term of this patent is extended or adjusted under 35 U.S.C. 154(b) by 195 days.

(21) Appl. No.: 14/376,355

(22) PCT Filed: Feb. 1, 2013

(86) PCT No.: PCT/EP2013/052032
§ 371 (c)(1),
(2) Date: Aug. 1, 2014

(87) PCT Pub. No.: WO2013/117497
PCT Pub. Date: Aug. 15, 2013

(65) Prior Publication Data
US 2015/0009320 A1    Jan. 8, 2015

Related U.S. Application Data

(60) Provisional application No. 61/596,038, filed on Feb. 7, 2012, provisional application No. 61/757,510, filed on Jan. 28, 2013.

(51) Int. Cl.
*G01M 11/00*        (2006.01)
*G01N 21/896*      (2006.01)
(Continued)

(52) U.S. Cl.
CPC ............ *G01M 11/30* (2013.01); *G01M 11/35* (2013.01); *G01M 11/37* (2013.01); *G01N 21/896* (2013.01);
(Continued)

(58) Field of Classification Search
CPC ......... G01N 2021/9511; G01N 21/958; G01N 2021/8832; G01N 21/896; G01N 21/952;
(Continued)

(56) References Cited

U.S. PATENT DOCUMENTS 4,304,489 A    12/1981   Wakabayashi
5,172,421 A    12/1992   Nakamura et al.
(Continued)

FOREIGN PATENT DOCUMENTS

CN    1938580 A    3/2007
DE    42 26 203    2/1994
(Continued)

OTHER PUBLICATIONS

International Search Report and Written Opinion for International Application No. PCT/EP2013/052032 dated Jun. 20, 2013 (16 pages).

*Primary Examiner* — Zhihan Zhou
(74) *Attorney, Agent, or Firm* — Merchant & Gould P.C.

(57) ABSTRACT

A visual inspection system (100, 200) for optical fibers (150) includes at least a pattern source (120, 220A, 220B, 220C, 520); at least a first illumination source (130, 230A, 230B, 230C, 510, 522) to direct light towards an optical fiber (150); and at least a first camera (140, 240A, 240B, 240C, 540) positioned at an opposite side of the fiber (150) from the pattern source (120, 220A, 220B, 220C, 520). At least one image (170, 180, 190) of the optical fiber (150) is taken and a pattern visible through the optical fiber (150) in the image (170, 180, 190) may be analyzed to detect distortions in the pattern.

18 Claims, 13 Drawing Sheets

(51) Int. Cl.
*G01N 21/958* (2006.01)
*G06T 7/00* (2017.01)
*G01N 21/952* (2006.01)
*G01N 21/88* (2006.01)
*G01N 21/95* (2006.01)

(52) U.S. Cl.
CPC ......... *G01N 21/958* (2013.01); *G06T 7/0008* (2013.01); *G01N 21/952* (2013.01); *G01N 2021/8832* (2013.01); *G01N 2021/9511* (2013.01); *G06T 2207/10004* (2013.01); *G06T 2207/10016* (2013.01); *G06T 2207/10152* (2013.01); *G06T 2207/30108* (2013.01)

(58) Field of Classification Search
CPC ...... G01M 11/37; G01M 11/30; G01M 11/35; G06T 2207/30108; G06T 7/0008; G06T 2207/10004; G06T 2207/10016; G06T 2207/10152
USPC .......................................................... 348/128
See application file for complete search history.

(56) References Cited

U.S. PATENT DOCUMENTS

| | | | | |
|---|---|---|---|---|
| 5,684,642 | A * | 11/1997 | Zumoto | B23K 26/032 359/739 |
| 5,953,113 | A | 9/1999 | Poffenbarger | |
| 6,122,045 | A | 9/2000 | Pike et al. | |
| 6,433,910 | B2 * | 8/2002 | Suga | 359/212.1 |
| 6,570,651 | B1 | 5/2003 | Haubold et al. | |
| 7,113,626 | B1 * | 9/2006 | Dar | G01M 11/37 382/141 |
| 7,522,277 | B2 | 4/2009 | Lehn et al. | |
| 2002/0054285 | A1 * | 5/2002 | Todo | G01M 11/088 356/73.1 |
| 2004/0012771 | A1 * | 1/2004 | Ehbets | G01C 1/02 356/4.01 |
| 2004/0066505 | A1 * | 4/2004 | Berg | G01N 21/952 356/237.1 |
| 2005/0259308 | A1 * | 11/2005 | Itoh | G02B 27/0905 359/211.2 |
| 2007/0188739 | A1 * | 8/2007 | Aoshima | G01M 11/37 356/73.1 |
| 2008/0144044 | A1 * | 6/2008 | Ehrick | G01B 11/25 356/610 |
| 2010/0290694 | A1 * | 11/2010 | Dubois | G01B 11/2527 382/141 |

FOREIGN PATENT DOCUMENTS

| | | |
|---|---|---|
| DE | 197 13 973 | 10/1998 |
| DE | 198 13 073 | 9/1999 |
| DE | 103 12 051 | 9/2004 |
| EP | 0 506 401 | 9/1992 |
| EP | 0 766 082 | 4/1997 |
| EP | 1 980 843 | 10/2008 |
| JP | 8-285790 | 11/1996 |
| JP | 2006-267022 A | 10/2006 |
| WO | WO 93/03350 | 2/1993 |
| WO | WO 03/016854 | 2/2003 |
| WO | WO 2005/095930 | 10/2005 |
| WO | WO 2005/095930 A1 | 10/2005 |
| WO | WO 2007/131257 | 11/2007 |

* cited by examiner

VISUALLY INSPECTING OPTICAL FIBERS

This application is a National Stage Application of PCT/EP2013/052032, filed 1 Feb. 2013, which claims benefit of U.S. Provisional Ser. No. 61/596,038, filed 7 Feb. 2012 and U.S. Provisional Ser. No. 61/757,510, filed 28 Jan. 2013 and which applications are incorporated herein by reference. To the extent appropriate, a claim of priority is made to each of the above disclosed applications.

BACKGROUND

Optical fibers may be contaminated and/or damaged during the manufacturing process. For example, the optical fibers may chip, crack, or splinter during a cleaving process. Other processes, such as stripping, cleaning, etc., may leave particulate or fluid contaminants on the fibers. Such damage and/or contamination can reduce signal quality of optical signals carried over the optical fibers. Damage and/or contaminants also may cause problems when the optical fibers are terminated at optical connectors or when the optical fibers are mated/demated with other optical fibers.

SUMMARY

Aspects of the disclosure related to a method for visually inspecting optical fibers including positioning an optical fiber so that a pattern source produces a pattern visible through the optical fiber when viewed through an annular side of the optical fiber; positioning an imaging sensor so that the optical fiber is disposed between the imaging sensor and the pattern source; obtaining at least one image of at least a portion of an annular surface of the optical fiber using the imaging sensor; and analyzing the pattern which is at least partially visible through the annular surface of the optical fiber in the image to detect distortions in the pattern.

Aspects of the disclosure related to a visual inspection system by which optical fibers are inspected for contamination or damage, the visual inspection system including a securement arrangement configured to retain an optical fiber; at least a first pattern source that produces a pattern; and at least a first imaging sensor positioned at an opposite side of optical fiber from the first pattern source. The first pattern source is positioned so that the pattern faces the optical fiber. The first imaging sensor is configured to obtain at least one image of any optical fiber held in front of the first pattern source.

Aspects of the disclosure related to a method for visually inspecting optical fibers including shining an axial illumination source along a longitudinal axis of an optical fiber; positioning a sensor so that the sensor detects light directed radially outwardly from the optical fiber; obtaining feedback from the sensor while the illumination source is shining on the optical fiber; and analyzing the feedback to detect contamination on the optical fiber.

Aspects of the disclosure related to a visual inspection system by which optical fibers are inspected for contamination or damage. The visual inspection system includes an axial illumination source positioned along a longitudinal axis of an optical fiber; and at least a first sensor positioned so as to receive light from an annular side of the optical fiber to detect contamination on the optical fiber.

Aspects of the disclosure related to a method for visually inspecting optical fibers using an optical monoblock reflector. The method includes disposing an optical fiber within an axial passage extending partially through the optical monoblock reflector; shining an illumination source towards the optical fiber; positioning a sensor relative to the optical monoblock reflector so that the optical monoblock reflector directs light from the fiber towards the sensor; obtaining feedback from the sensor while the illumination source is shining on the optical fiber; and analyzing the feedback to detect contamination or damage. The optical passage extends from an open end of the optical monoblock reflector to a conical section.

Aspects of the disclosure related to a visual inspection system by which optical fibers are inspected for contamination or damage. The visual inspection system includes a monoblock reflector defining an axial passage extending inwardly from a first end of the monoblock reflector. The axial passage is configured to receive at least a portion of an optical fiber. The visual inspection system also includes an illumination source positioned to shine light on any optical fiber positioned in the axial passage; and a sensor positioned so that at least a portion of the monoblock reflector is located between the sensor and the optical fiber. The sensor is configured to receive light directed from an annular surface of the optical fiber from the monoblock reflector.

A variety of additional aspects will be set forth in the description that follows. These aspects can relate to individual features and to combinations of features. It is to be understood that both the foregoing general description and the following detailed description are exemplary and explanatory only and are not restrictive of the broad concepts upon which the embodiments disclosed herein are based.

DETAILED DESCRIPTION

Reference will now be made in detail to the exemplary aspects of the present disclosure that are illustrated in the accompanying drawings. Wherever possible, the same reference numbers will be used throughout the drawings to refer to the same or like structure.

Figure 1:
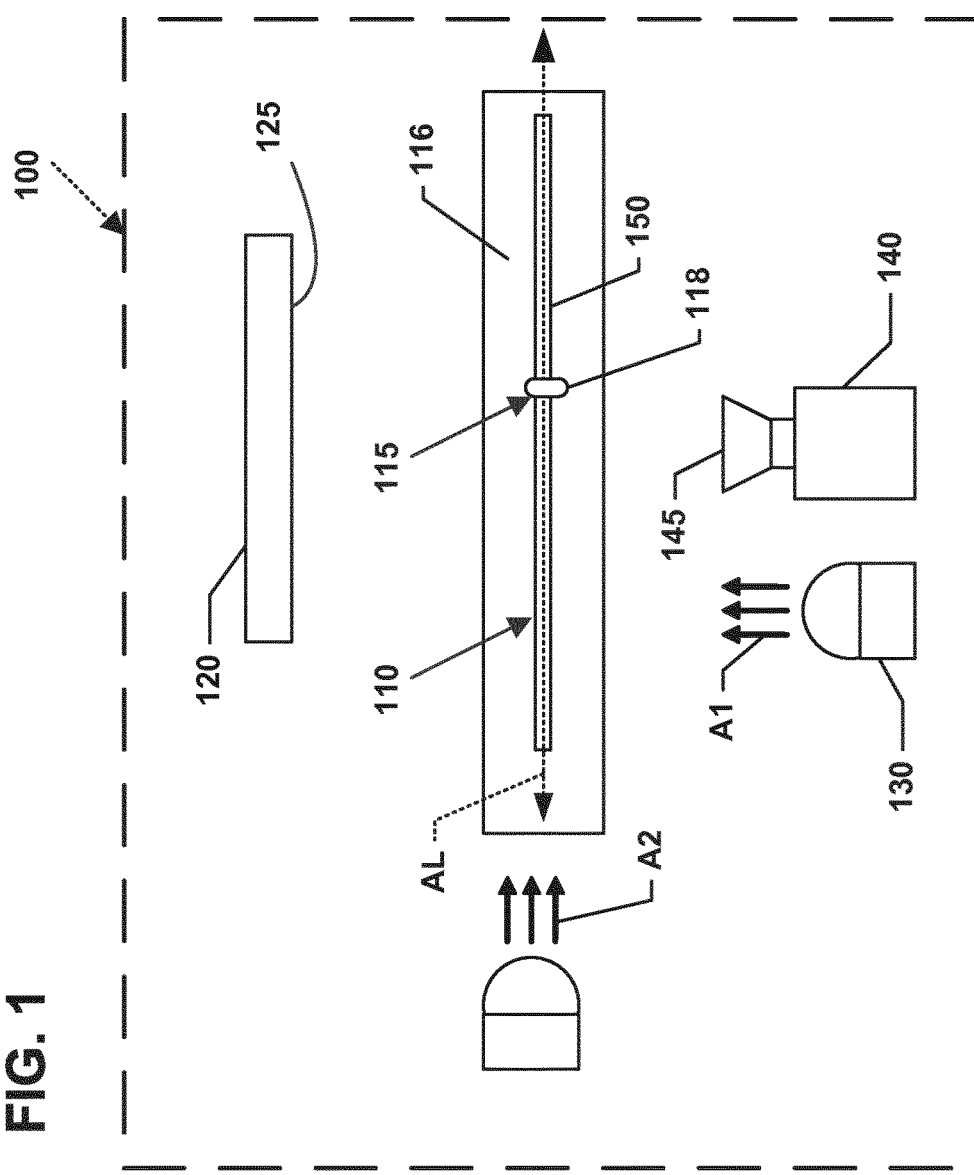
FIG. 1 is a schematic diagram of an example visual inspection system for optical fibers having a screen, a camera, and two illumination sources.

FIG. 1 is a schematic diagram showing a visual inspection system 100 by which optical fibers 150 may be inspected for contamination and/or damage. The example visual inspection system 100 includes a fiber securement arrangement 115 defining a securement location 110, a pattern source 120, an illumination source, and a camera 140.

The fiber securement arrangement 115 is configured to retain an optical fiber 150 at the securement location 110. In certain implementations, the fiber securement arrangement 115 includes a table, platform, or other base 116 and one or more clamps 118. In other implementations, the fiber securement arrangement 115 includes a channel or slot defined in the base 116. In still other implementations, the fiber securement arrangement 115 includes a vacuum pump and suction holes defined in the base 116. In other implementations, the fiber securement arrangement 115 is otherwise configured to hold the fiber optic cable 150 in place.

The pattern source 120 displays a pattern. In some implementations, the pattern source 120 includes a screen 120 having a patterned surface 125. In other implementations, the pattern source 120 may include another illumination source that emits a light pattern. In still other implementations, the pattern source 120 may include a surface having transparent sections and non-transparent sections arranged in a pattern so that a pattern of light is created when the surface is illuminated from behind. For ease in understanding, the following disclosure will refer to the pattern source 120 as a screen 120 with a pattern printed on the surface 125. It is to be understood, however, that any source configured to produce a visible pattern that may be imaged through the optical fiber 150 may be utilized with any of the systems and processes disclosed herein.

The screen 120 is positioned so that the patterned surface 125 faces the securement location 110. In certain implementations, the patterned surface 125 defines a non-uniform pattern. The screen 120 is positioned at a location spaced from the fiber securement arrangement 115. The screen 120 is positioned and oriented to extend along parallel to the longitudinal axis AL of any optical fiber 150 held at the securement location 110 so that a peripheral sidewall (e.g., an elongated annular sidewall) of the optical fiber 150 extends in front of the patterned surface 125.

Figure 2:
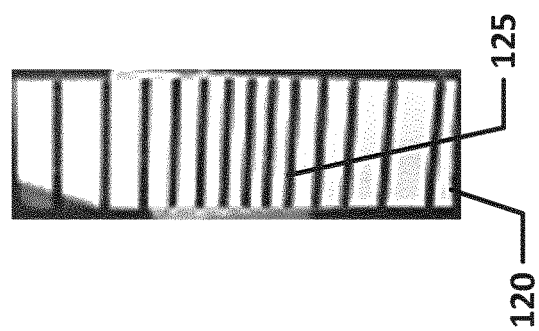
FIG. 2 illustrates one example patterned surface suitable for any of the screens disclosed herein.

In some implementations, the patterned surface 125 includes a plurality of stripes (e.g., see FIG. 2). In certain implementations, the stripes of the patterned surface 125 extend parallel to the longitudinal axis AL of any optical fiber 150 that is retained at the securement location 110. In certain implementations, the stripes are of uniform thickness. In other implementations, the stripes at the center of the screen 120 may have a different thickness than the stripes at edges of the screen 120. In certain implementations, the stripes of the patterned surface 125 are denser at a center of the patterned surface 125 and more spaced out at the top and bottom of the patterned surface 125. For example, such a pattern, when seen through the examined fiber, may exhibit an even, uniform distribution of the stripes forming the visible pattern due to the lensing effect. In other implementations, the stripes may be oriented perpendicular to or otherwise at an angle to the longitudinal axis AL. In still other implementations, the patterned surface 125 defines some other type of pattern.

The illumination source is configured to provide light to illuminate the optical fiber 150. In some implementations, the illumination source includes a radial illumination source 130 that directs light towards the patterned surface 125 of the screen 120. In other implementations, the illumination source includes an axial illumination source 160 that directs light along the longitudinal axis AL of the optical fiber 150. In some implementations, the illumination source includes at least a first LED. In certain implementations, the illumination source includes multiple LEDs. In other implementations, the illumination source includes a halogen light, a fluorescent light, or any other light source.

The radial illumination source 130 is positioned relative to the securement location 110 so that the first illumination source 130 directs light towards the patterned surface 125 of the screen 120. In certain implementations, the first illumination source 130 does not direct light directly towards the optical fiber 150. In certain implementations, the first illumination source 130 does direct light towards the optical fiber 150 as well as the screen 120. In certain implementations, the securement location 110 is disposed between the radial illumination source 130 and the screen 120. For example, in certain implementations, the radial illumination source 130 and optical fiber 150 may be in-line with the screen 120. In other implementations, the radial illumination source 130 may be offset from an axis extending between the fiber 150 and the screen 120.

The camera 140 is positioned and oriented to obtain images (e.g., images 170, 180, 190) of at least a portion of any optical fiber 150 disposed at the securement location 110. In some implementations, the camera 140 is directed along a radial axis of the optical fiber 150 to obtain one or more images of the peripheral sidewall of the optical fiber 150. In certain implementations, the camera 140 also is positioned so that the patterned surface 125 of the screen 120 forms a background for the optical fiber 150 in the images. In certain implementations, the camera 140 is positioned at an opposite side of the securement location 110 from the first screen 120. In certain implementations, the camera 140 is positioned so that part of the patterned surface 125 is focused and/or magnified by the optical fiber 150 so that the part of the patterned surface 125 is visible through the optical fiber 150 in the obtained images.

In some implementations, the camera 140 includes a still-photograph camera that is configured to obtain one or more still images of the optical fiber 150. In other implementations, the camera 140 includes a video camera that is configured to obtain a continuous sequence of images over a duration of time. In some implementations, the camera 140 is stationary relative to the securement location 110. In other implementations, the camera 140 is configured to move relative to the securement location 110. In certain implementations, the camera 140 is configured to move while recording a video image. In other implementations, the camera 140 is configured to be repositioned between shots (i.e., when not obtaining images) so that images showing various parts and/or angles of the optical fiber 150 may be obtained.

A method for visually inspecting optical fibers 150 using the visual inspection system 100 of FIG. 1 includes mounting an optical fiber 150 to the fiber securement arrangement 115 so that a screen 120 extends parallel to the longitudinal axis AL of the optical fiber 150. In some implementations, the optical fiber 150 is positioned a sufficient distance from the screen 120 so that the patterned surface 125 is visible in the obtained images only through the optical fiber 150. For example, the patterned surface 125 of the screen 120 may appear to be a uniform gray instead of patterned around the fiber 150. In certain implementations, the screen 120 is positioned at a distance ranging from about 6 mm to about 20 mm.

The visual inspection method also includes shining an illumination source 130 along a first illumination axis A1 (FIG. 1) towards the optical fiber 150. In the example shown, the first illumination axis A1 of a first illumination source 130 extends radially towards the fiber 150. In other implementations, the illumination source 130 may shine axially or at a non-orthogonal angle relative to the longitudinal axis AL of the fiber 150. In still other implementations, multiple illumination sources 130 may be utilized to illuminate the screen 120 and/or the optical fiber 150 from various directions. The method also includes positioning a camera 140 so that the optical fiber 150 is disposed between a camera lens 145 (FIG. 1) of the camera 140 and the patterned surface 125 of the screen 120. In some implementations, the camera 140 is mounted to be stationary relative to the securement location 110. In other implementations, the camera 140 is secured in one of a plurality of possible positions relative to the securement location 110. In certain implementations, the camera 140 is positioned at an opposite side of the fiber 150 from the screen 120 so that at least a portion of the patterned surface 125 is visible through the optical fiber 150 from the position of the camera lens 145.

In some implementations, the camera 140 is positioned so that the camera lens 145 is spaced from the optical fiber 150 by a distance ranging between about 1 millimeter (mm) and about 500 mm. In certain implementations, the camera 140 is positioned so that the camera lens 145 is spaced from the optical fiber 150 by a distance ranging between about 5 mm and about 150 mm. In certain implementations, the camera 140 is positioned so that the camera lens 145 is spaced from the optical fiber 150 by a distance ranging between about 10 mm and about 40 mm. In certain implementations, the camera 140 is positioned no more than 60 mm from the fiber 150. In certain implementations, the camera 140 is positioned no more than 30 mm from the fiber 150. In one example implementation, the camera 140 is positioned about 20 mm away from the optical fiber 150.

The visual inspection method also includes obtaining at least one image (e.g., images 170, 180, 190) of at least a portion of the optical fiber 150 using the camera 140 while the illumination source 130 is shining on the optical fiber 150. In some implementations, the camera 140 obtains a single still image (e.g., a photograph) of the optical fiber 150 or portion thereof. In certain implementations, the camera 140 obtains a plurality of still images of the optical fiber 150. In other implementations, the camera 140 obtains one or more videos of the optical fiber 150 over a particular time duration (e.g., 1 milliseconds (ms), 5 ms, 7 ms, 10 ms, 15 ms, 20 ms, 25 ms, 30 ms, 35 ms, 40 ms, 50 ms, 60 ms, 100 ms, 150 ms, 200 ms, etc.).

In some implementations, an image showing the entire fiber 150 is obtained. In other implementations, each image obtains only a portion of the optical fiber 150. For example, in certain implementations, the field of view for the camera 140 is less than 50 mm of optical fiber 150. In certain implementations, the field of view for the camera 140 is less than 30 mm of optical fiber 150. In certain implementations, the field of view for the camera 140 is less than 20 mm of optical fiber 150. In certain implementations, the field of view for the camera 140 is less than 10 mm of optical fiber 150. In certain implementations, the field of view for the camera 140 is less than 5 mm of optical fiber 150. In one example implementation, the field of view is about 2 mm.

Figure 3:
FIG. 3 is a first example image, which shows a radially illuminated optical fiber having a chip, of the type that would be obtained using any of the visual inspection systems disclosed herein.
Figure 4:
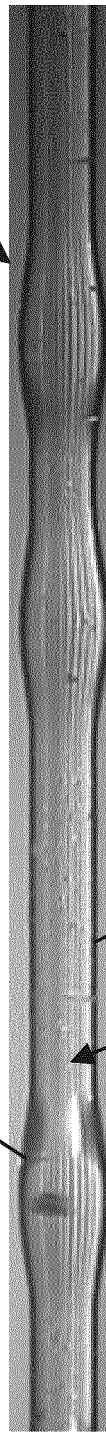
FIG. 4 is a first example image, which shows a radially illuminated optical fiber covered in a liquid contaminant, of the type that would be obtained using any of the visual inspection systems disclosed herein.
Figure 5:
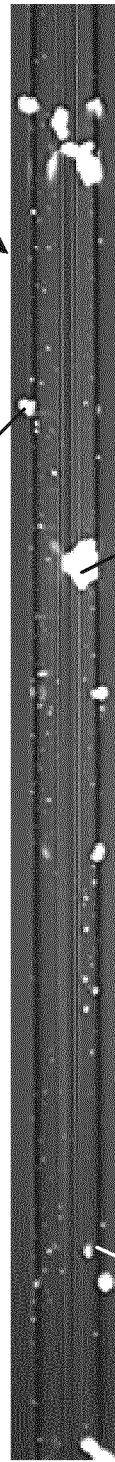
FIG. 5 is a first example image, which shows an axially illuminated optical fiber, of the type that would be obtained using any of the visual inspection systems disclosed herein.

The visual inspection method also includes analyzing a pattern 155 visible through the optical fiber 150 in the image or images to detect distortions in the pattern. Three examples images of optical fibers 150 are shown in FIGS. 3-5. FIG. 3 is an example still image 170 obtained using a radial illumination source 130. As shown, part 155 of the patterned surface 125 of the screen 120 is visible through the optical fiber 150. Damage to the optical fiber 150, such as a chip or broken edge 175, may be identified by changes in the visible pattern 155 seen in the fiber 150. FIG. 4 is another example still image 180 obtained using a radial illumination source 130. As shown, part 155 of the patterned surface 125 of the screen 120 is visible through the optical fiber 150. Non-scattering contamination on the optical fiber 150, such as a liquid contaminant 185 (e.g., cleaning solution), may be identified by changes in the visible pattern 155 seen in the fiber 150. For example, sections of the optical fiber 150 in FIG. 4 appear to bulge outward and the visible pattern 155 appears magnified at the bulges where liquid 185 is disposed on the fiber 150.

FIG. 5 is another example still image 190 obtained using an axial illumination source 160. Contamination on the optical fiber 150, such as particulate contaminants 195 (e.g., dust, coating debris left from stripping a primary coating from the fiber 150, etc.), may glow or otherwise become more identifiable (e.g., due to light scattering effects) when the fiber 150 is illuminated along the longitudinal axis AL of the fiber 150. In certain implementations, one or more radial illumination sources 130 also may be used and part 155 of the patterned surface 125 of the screen 120 may be visible through the optical fiber 150. Particulate contaminants 195 also may block or otherwise obstruct portions of the visible pattern 155 seen in the fiber 150, thereby identifying the particulate 195. Since the fiber 150 is transparent and acting as a cylindrical lens, contaminants 195 disposed at an opposite side of the fiber 150 from the camera 140 will still be visible. Light is characterized by direction/distribution, spectral content (color), temporal distribution (such as pulsed), and polarization. The above described imaging processes focus on the direction/distribution characterizations. In other implementations, the imaging analysis may be performed using processes directed to other characterizations instead of or in addition to the above described analyses. For example, in some implementations, polarized illumination light may be used in combination with polarization filters to record the images.

In some implementations, the imaging sensor 140 may obtain multiple images of the optical fiber 150 and the pattern visible through the fiber 150.

Each of the images may record a different portion of the pattern 125 (or different pattern) illuminated in a different color (e.g., a color with which only one of the patterns or potions thereof has a high contrast). Alternatively, in certain implementations, the patterns (or portions thereof) can be recorded in a single color image with color separation being achieved via color channels of the imaging sensor. In addition, some problems with small depth-of-field may be mitigated using light of different wavelengths in combination with suitable dispersion of the camera lens (or other elements in the imaging path).

Accordingly, in some implementations, portions of the pattern 125 may be formed in one or more colors. For example, in certain implementations, one or more stripes in an example pattern 125 may be formed in a different color from another of the stripes. In some implementations, one or more illumination sources 130, 160 may produce white light. In other implementations, however, one or more illumination sources 130, 160 may produce light shaded a particular color. In some implementations, the imaging sensor 140 is configured to produce monochrome images. In other implementations, the imaging sensor 140 is configured to produce color images.

In some implementations, fluorescence imaging can be used to detect/identify contaminants (e.g., liquid and/or particulate) on the optical fiber 150. In general, the range of optical wavelength at which the fiber 150 is imaged can be different from the wavelength range at which it is illuminated (e.g., by illumination sources 130, 160). This restricted range of optical wavelengths in the image can be achieved by including an optical filter (e.g., a long-pass filter, a band-pass filter, or a short-pass filter) in the camera to block the illumination light at least partially. Fluorescence imaging also can be achieved by using pulsed illumination and timing the exposure of the camera to record an image after the illumination pulse (while fluorescence light is still emitted from contaminants).

Figure 6:
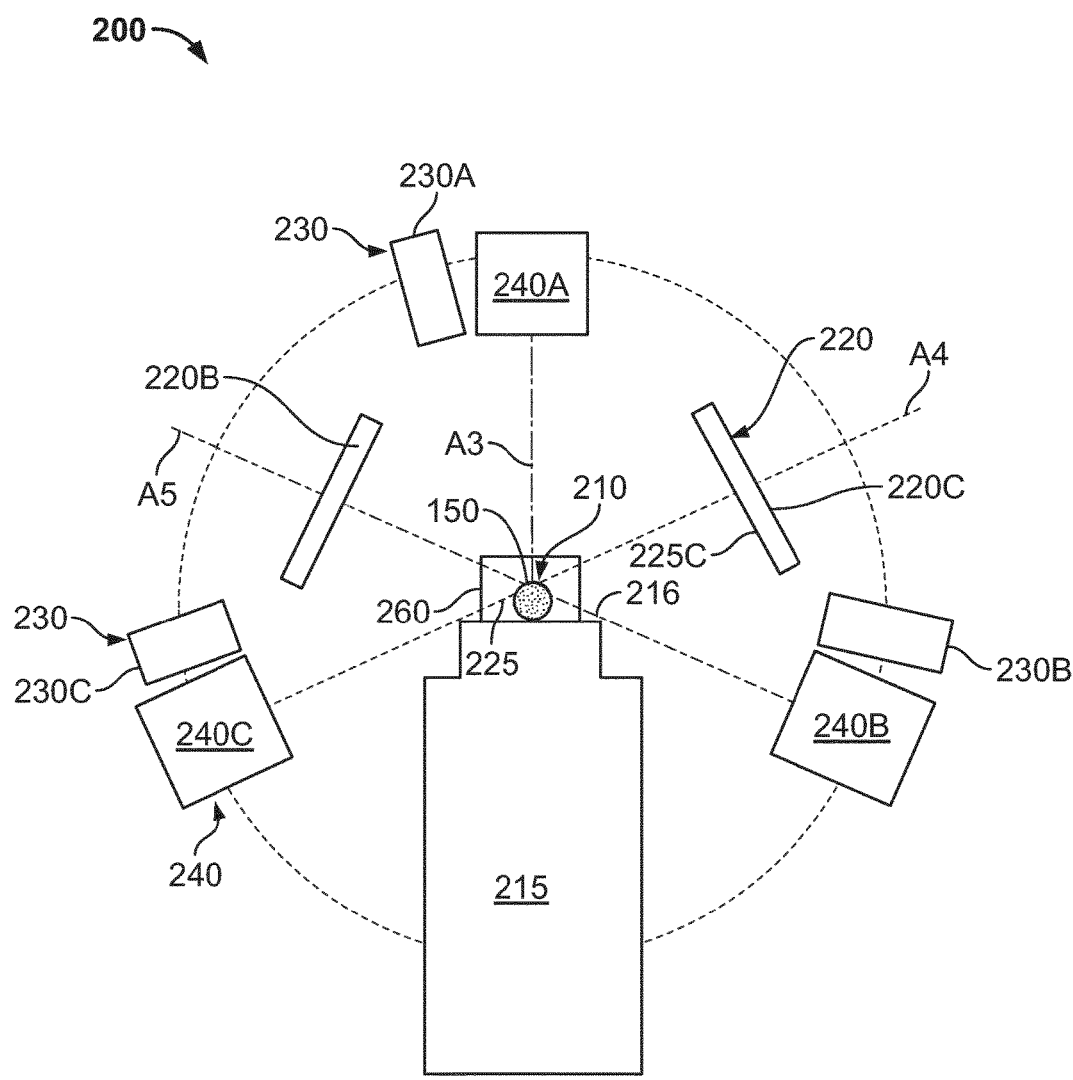
FIG. 6 is a schematic diagram of another example visual inspection system for optical fibers having a screen at multiple positions, a camera at multiple positions, and multiple illumination sources.

FIG. 6 is a schematic diagram showing another example visual inspection system 200 by which optical fibers 150 may be inspected for contamination and/or damage. The example visual inspection system 200 includes a fiber securement arrangement 215 defining a securement location 210, at least a first screen 220, at least a first illumination source 230, and at least a first camera 240.

The fiber securement arrangement 215 is oriented in FIG. 6 so that the reader is looking down the longitudinal axis of an optical fiber 150 held at the securement location 210.

In general, the cameras 240, screens 220, and illumination sources 230 of FIG. 6 function in the same or a similar manner to the corresponding components 140, 120, 130 of the visual inspection system 100 of FIG. 1. In some implementations, the fiber securement arrangement 215 is generally the same as fiber securement arrangement 115 of FIG. 1. In other implementations, however, the fiber securement arrangement 215 may be otherwise configured to retain an optical fiber 150 in place.

In accordance with some aspects of the disclosure, it is desirable to obtain multiple images of an optical fiber 150 showing the fiber 150 from different sides and/or angles (e.g., due to the lensing effect of the fiber 150). For example, bright spots produced by particulate contaminants may appear to have a different size and/or intensity when viewed from a first side of the fiber 150 (e.g., the side on which the particulate 195 is disposed) than when viewed from a second side of the fiber 150 (e.g., the opposite side of the fiber 150 from where the particulate 195 is disposed).

In some implementations, multiple images may be obtained using multiple cameras. For example, the visual inspection system 200 shown in FIG. 6 includes a first camera 240A, a second camera 240B, and a third camera 240C. In other implementations, however, the visual inspection system 200 may include a greater or lesser number of cameras. In some implementations, each camera 240A-240C has a corresponding screen 220A-220C positioned at an opposite side of the securement location 210 from the camera 240A-240C. In other implementations, a single screen may be movable relative to the securement location 210 to be selectively positioned opposite each camera 240A-240C.

In some implementations, each camera 240A-240C has its own illumination source 230A-230C. In certain implementations, the illumination source 230A-230C may be integral with the camera 240A-240C. In other implementations, the illumination source 230A-230C may be generally aligned with the camera 240A-240C (see FIG. 6). In still other implementations, the illumination source 230A-230C may be offset from the respective camera 240A-240C. In some implementations, each camera 240A-240C has multiple illumination sources. For example, each camera 240A-240C may have multiple LEDs associated with it. In other implementations, each camera 240A-240C has a corresponding radial illumination source 230A-230C and the visual inspection system 200 also has an axial illumination source 260. In still other implementations, one or more illumination sources 230A-230C may be movable relative to the securement location 210 to selectively position the illumination sources 230A-230C depending on the image to be taken and the camera 240A-240C to be used.

In some implementations, each camera 240A-240C is directed along a different radial axis of the optical fiber 150. In the example shown in FIG. 6, a first camera 240A and a first illumination source 230A are positioned above the optical fiber 150 opposite a base of the fiber securement arrangement 215. The camera lens of the first camera 240A is directed along a first radial axis A3. A second camera 240B and a second illumination source 230B are circumferentially offset from the first camera 240A and illumination source 230A by about 120°. The camera lens of the second camera 240B is directed along a second radial axis A4. A third camera 240C and a third illumination source 230C are circumferentially offset from the first camera 240A and illumination source 230A and from the second camera 240B and illumination source 230B by about 120°. The camera lens of the third camera 240C is directed along a third radial axis A5. In other implementations, the cameras 240A-240C are spaced at other circumferential locations about the optical fiber 150 (e.g., no more than 60° apart, no more than 90° apart, no more than 45° apart).

In some implementations, each camera 240A-240C has its own screen 220A-220C. In some such implementations, the patterned surface 225A of the first screen 220A is disposed at the securement location 210 (e.g., printed on a base on which the fiber 150 is positioned). In other such implementations, the patterned surface 225A of the first screen 220A is disposed at a location spaced beneath the fiber 150. The second and third screens 220B, 220C are located at opposite sides of the securement location 210 from the respective cameras 240B and 240C. In other implementations, a single screen may be movable relative to the securement location 210 to be selectively positioned opposite the camera position.

In other implementations, multiple images may be obtained using the same camera, screen, and/or illumination source. For example, a camera 240, screen 220, and illumination source 230 may be moved relative to the fiber securement location 210 between multiple positions. In some implementations, the camera 240 may be moved to any of the camera positions shown in FIG. 6 (e.g., see camera position 240A, camera position 240B, and camera position 240C). In other implementations, the camera 240 may be moved to any other position from which it may be directed radially towards the peripheral sidewall of the optical fiber 150. In certain implementations, the camera 240 also may be moved to a position along the longitudinal axis of the optical fiber 150 to image a cleaved end of the optical fiber 150 (e.g., to inspect for damage and/or alignment).

In some implementations, the camera 240 is configured to rotate to various circumferential positions about the optical fiber 150 while remaining fixed relative to an axial length of the fiber 150. In other implementations, the camera 240 also is configured to move along the axial length of the optical fiber 150. For example, the camera 240 may move along the axial length of the fiber 150 so that additional portions of the optical fiber 150 enter the field of view of the camera 240. Accordingly, moving the camera 240 along the axial length of the fiber 150 provides imaging of a greater portion of the optical fiber 150. In certain implementations, the camera 240 is moved so that the obtained images may be combined together to form a more complete view of the optical fiber 150. For example, the camera 240 may be moved by a distance corresponding to the field of view of the camera 240.

Figure 7:
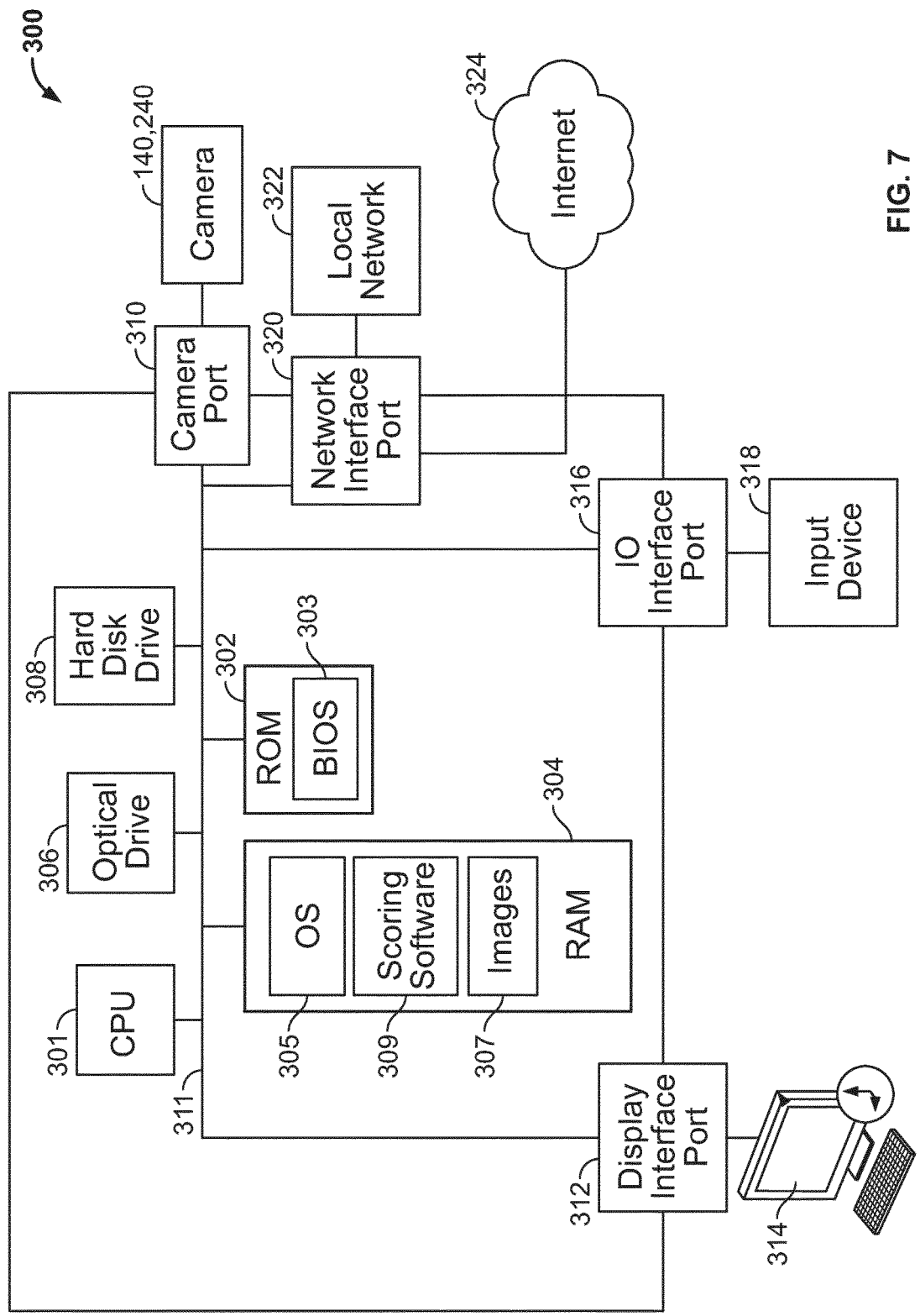
FIG. 7 is a schematic block diagram of a computer configured to obtain images from a camera and display the images to a user.

Referring to FIG. 7, any of the cameras 140, 240 disclosed herein may be coupled to a computer system 300 (e.g., a desktop computer, a laptop computer, a networked terminal, a server computer, a specialized microcontroller, a smartphone or other personal digital assistant, etc.). The computer 300 includes a processor 301 and memory. For example, the computer 300 includes Read Only Memory (ROM) 302 that stores BIOS data 303. The computer 300 also includes Random Access Memory (RAM) 304, which may store an operating system 305. The ROM 302 and RAM 304 are accessible by the processor 301. The computer 300 also may include other types of memory (e.g., one or more optical drives 306, one or more hard disk drives 308, etc.).

The computer 300 also may include a display interface port 312 that enables the computer 300 to connect to a display device 314 (e.g., a digital screen, a monitor, a speaker, a printer, a projector, etc.). The computer 300 also may include an IO interface port 316 that enables the computer to connect to an input device 318 (e.g., a mouse, a keyboard, a microphone, a touchscreen, buttons, flywheel, keypad, joystick, or any other type of sensor or controller). The computer 300 also may include a network interface port 320 that is configured to connect the computer 300 to a local area network 322 and/or to the Internet 324.

The computer 300 also includes a camera interface port 310 at which one or more cameras 140, 240 of any of the systems disclosed herein may be coupled. The processor 301 communicates with the camera 140, 240 to obtain (e.g., download) images taken with the camera 140, 240. In some implementations, the processor 301 communicates with the camera 140, 240 automatically when the camera 140, 240 is connected to the computer 300, at a scheduled time, etc.). In other implementations, the processor 301 communicates with the camera 140, 240 in response to input entered at the input device 318. In some implementations, the processor 301 stores the images 307 obtained from the camera 140, 240 in memory (e.g., to RAM 304). In other implementations, the processor 301 displays the images obtained from the camera 140, 240 on the display device 314. In certain implementations, the processor 301 obtains the storage images 307 from memory to display on the display device 314.

In some implementations, a user visually inspects the displayed images to determine whether the optical fiber 150 is damaged and/or contaminated. For example, a user may view one or more of the obtained images 307 on the display device 314 and determine whether damage and/or contamination is visible. In certain implementations, the user may count a number of bright spots on the fiber 150 that indicate debris. In certain implementations, the user may count a number of chips, scratches, and/or splinters. In certain implementations, the user may count a number of distortions in the pattern visible in the fiber 150 or otherwise determine the quality of the visible pattern. In certain implementations, the user may determine the total number of white pixels (e.g., pixels forming the bright spots) in the image. In certain implementations, the user may measure each of the bright spots in the image. In one example implementation, the user may determine the dimensions of the largest bright spot in each image. In another example implementation, the user may determine the average dimensions of the bright spots in each image.

In other implementations, the processor 301 implements scoring software 309 to determine whether the optical fiber 150 is damaged and/or contaminated. In the example shown, the scoring software 309 is stored in the RAM 304 of the computer 300. In other implementations, however, the scoring software 309 may be stored elsewhere in memory (e.g., the optical drive 306, the hard drive 308, etc.) or at a remote site connected via a network (e.g., local network 322 or the Internet 324).

Figure 8:
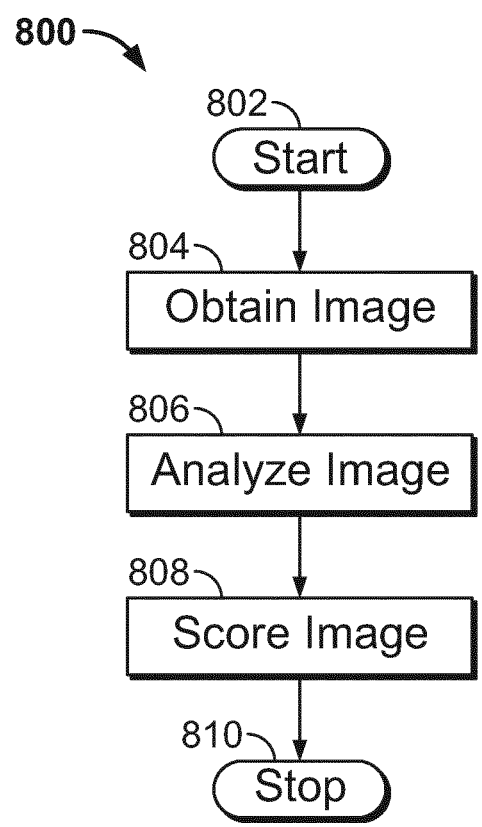
FIG. 8 is a flowchart illustrating an example scoring process that may be implemented by the processor of computer when automatically inspecting an optical fiber.

FIG. 8 is a flowchart illustrating an example scoring process 800 that may be implemented by the processor 301 of computer 300 (FIG. 7) when automatically inspecting an optical fiber 150. The scoring process 800 begins at a start module 802, performs any appropriate initialization procedures, and proceeds to an obtain operation 804.

At the obtain operation 804, the processor 301 obtains one or more images 307 of the fiber. In some implementations, the obtain operation 804 includes accessing the RAM 304 or other memory and pulling the images 307 from memory. In other implementations, the obtain operation 804 includes accessing memory of the camera 140, 240 and pulling the images from the camera memory.

At an analyze operation 806, the processor 301 causes the scoring software 309 to examine the images 307 to detect contamination and/or damage. For example, in certain implementations, the scoring software 309 may identify and count and/or measure a number of bright spots in the image 307, which may indicate debris on the optical fiber. For example, the scoring software 309 may implement any of the analysis processes described above with respect to the manual user inspection. In certain implementations, the scoring software 309 may compare the pattern visible through the optical fiber 150 in the image 307 to one or more control images of the pattern and determine a distortion level. In certain implementations, the scoring software 309 may determine a type of distortion (e.g., blurred pattern, stretched pattern, pattern sections missing, etc.) to determine how the fiber 150 is contaminated or damaged (e.g., particle contaminants, liquid contaminants, chips, etc.).

At a score operation 808, the processor 301 causes the scoring software 309 to determine whether the fiber 150 passes or fails inspection. In some implementations, the scoring software 309 compares the number and/or size of identified particle contaminants to predetermined thresholds for amount and size to determine whether the fiber 150 passes inspection. In other implementations, the scoring software 309 compares a distortion level of the pattern to predetermined thresholds for distortion level. In still other implementations, the scoring software 309 compares the number and/or size of the identified chips, splinters, or other damage to predetermined thresholds.

In certain implementations, the scores of multiple images of the same fiber 150 may be averaged together or otherwise taken into account when determining an overall score for the fiber 150. In certain implementations, the scoring software 309 may be taught how to score the images 307. For example, the software 309 may analyze a plurality of images that were manually scored. The software 309 stores scoring parameters based on the analysis and applies the stored parameters to subsequent images. In other implementations, the software 309 is capable of continuously improving the scoring accuracy by using feedback from data (e.g., automatically transferred data) of other sensors in the fiber processing sequence.

Referring to FIGS. 9-14, an optical monoblock reflector or other optical lens system may be used in combination with one or more cameras (e.g., any of cameras 140, 240 or another type of camera), one or more screens (e.g., any of screens 120, 220 or another type of screen), and one or more illumination devices (e.g., any of illumination devices 130, 160, 230, 260 or another type of illumination device) to obtain images of the fiber 150 efficiently. In some implementations, the illumination device directs light axially along the fiber 150. In other implementations, the illumination device directs the light radially towards internal facets of the monoblock and/or towards the fiber 150. The monoblock reflector will allow a redirection of light from the fiber 150 to various system components.

Figure 9:
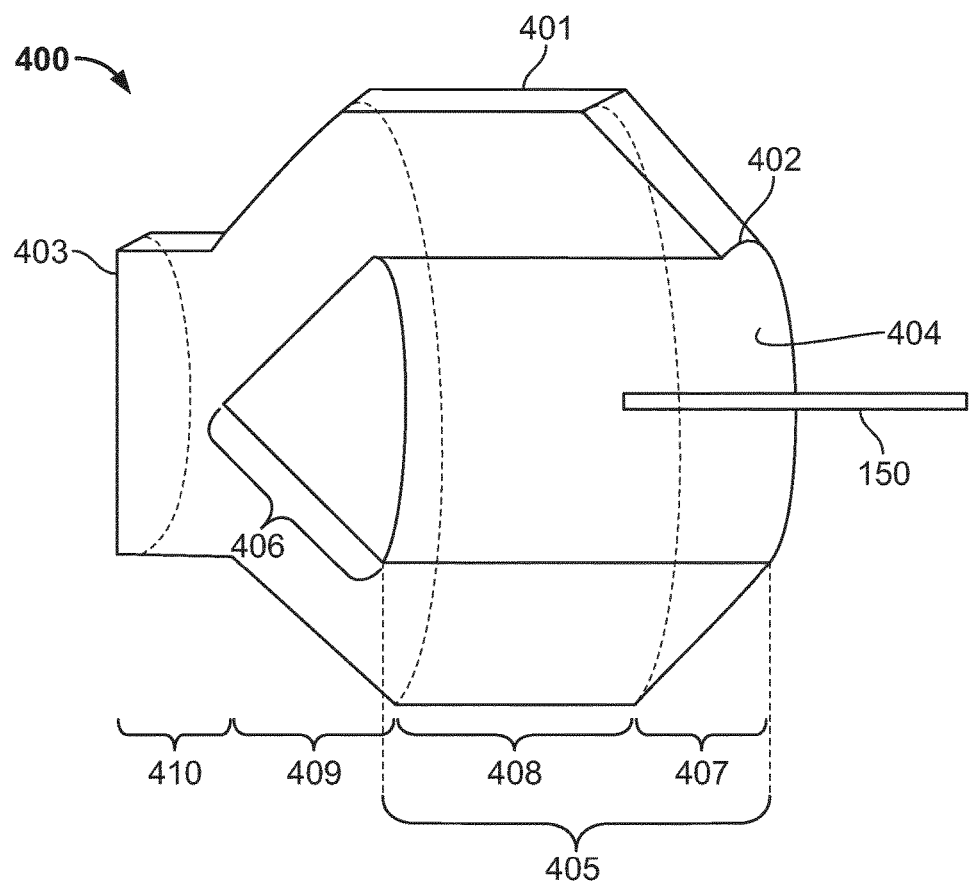
FIG. 9 is a cross-sectional view of an example optical monoblock reflector.

FIG. 9 is a cross-sectional view of an optical monoblock reflector 400 having a body 401 extending from a first end 402 to a second end 403. The body 401 is formed of a transparent material (e.g., glass, transparent plastic, etc.) and includes multiple reflective surfaces. The body 401 has a first conically-shaped section 407 that tapers outwardly from the first end 402 towards the second end 403, a generally cylindrically-shaped second section 408, a third conically-shaped section 409 that tapers inwardly from the second section 408 towards the second end 403, and a generally cylindrically-shaped fourth section 410.

The body 401 defines an axial passage 404 extending partially through the body 401 from the first end 402. The passage 404 has a generally cylindrical section 405 extending inwardly from the first end 402 of the body 401 and terminating at a conical section 406 that tapers inwardly towards the second end 403 of the body 401. The cylindrical section 405 of the passage 404 extends through the first and second sections 407, 408 of the body 401. The conical section 406 of the passage 404 generally extends axially along the third section 409 of the body 401. The fourth section 410 of the body 401 is generally solid.

Figure 10:
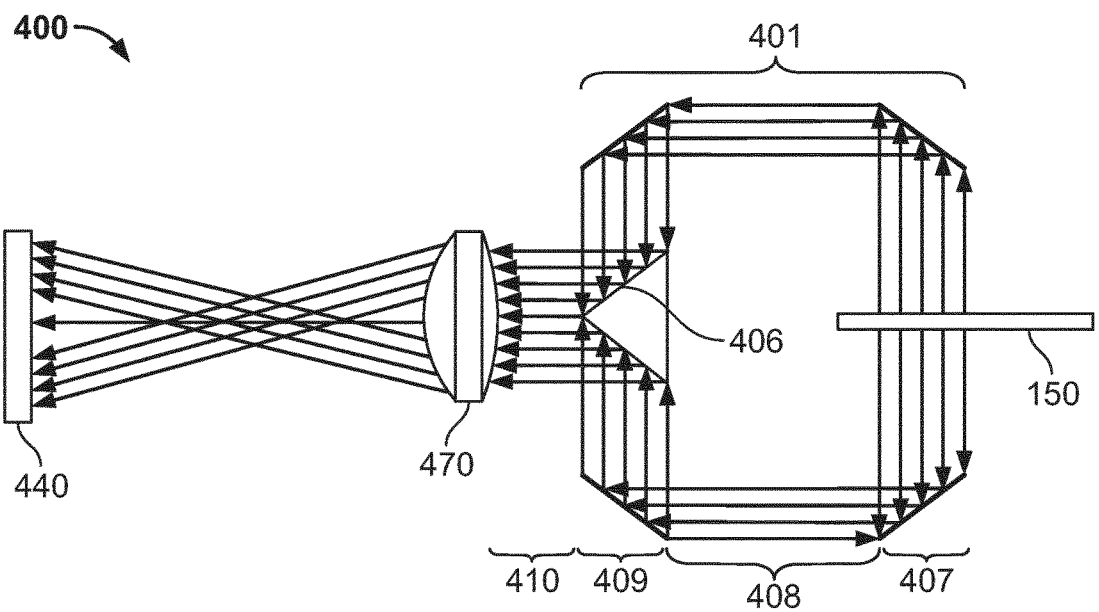
FIG. 10 is a schematic diagram illustrating how light reflects off the optical fiber and into the monoblock body of FIG. 9 when an optical fiber is positioned within the passage of the monoblock body.

When an optical fiber 150 is inserted into the passage 404 from the first end 402 of the body 401, light reflects off the fiber 150 and into the monoblock body 401 as shown schematically in FIG. 10. The light is received at an interior of the first section 407 of the body 401 and reflects off the tapered walls towards the second end 403 of the body 401. The light reflects off the tapered walls of the third section 409 of the body 401 and towards the tapered walls of the conical passage section 406. The conical passage section 406 directs the light through the fourth section 410 of the body 401 and out of the monoblock 400. In some implementations, the light reflects off the tapered surfaces due to Fresnel reflection or (total) internal reflection. In other implementations, a reflective coating may be applied to the tapered surfaces.

The light leaving the monoblock body 401 is directed towards a sensor 440. In some implementations, the light is directed towards a single light sensor (e.g., a photo resistor, phototransistor, or photodiode). In other implementations, the light is directed towards a plurality of sensors (e.g., an array of phototransistors or photodiodes). In still other implementations, the light may be directed towards one or more imaging sensors (e.g., a photographic camera, a video camera, a CCD/CMOS image sensors, etc.). The light reflected by the monoblock 400 onto the sensor 440 produces a circular image representing the circumference of the fiber 150 (or portion thereof disposed within the passage 404). In other words, the light reflected by the monoblock 400 onto the sensor 440 produces a 360° view of the optical fiber 150. Accordingly, multiple circumferential sides of the fiber 150 may be visually inspected using one image.

Since the image is taken from many (if not all) sides of the fiber 150 at once, the monoblock 400 improves the tolerance of the system. For example, the monoblock allows the sensor 440 to obtain one or more images of the fiber 150 even if the fiber 150 is misaligned within the passage 404, vibrating, or otherwise moving slightly. The monoblock reflector 400 advantageously increases efficiency by allowing a thorough visual inspection to occur with fewer images. Decreasing the number of images obtained per fiber increases the speed at which an individual fiber may be processed. Decreasing the number of images also may decrease the amount of equipment necessary to inspect the fiber. For example, the monoblock 400 allows a user to obtain images of multiple sides of the fiber 150 using a single, stationary sensor 440 instead of multiple cameras or a moveable camera.

In some implementations, the visual inspection process includes ascertaining an intensity of the light obtained from the monoblock 400. For example, the inspection process may include measuring and quantifying the intensity of scattered light produced by debris. In such systems, the sensor 440 may include a simple light detector. Accordingly, a more costly imaging sensor is not needed in such systems, thereby decreasing the cost of the systems.

Figure 11:
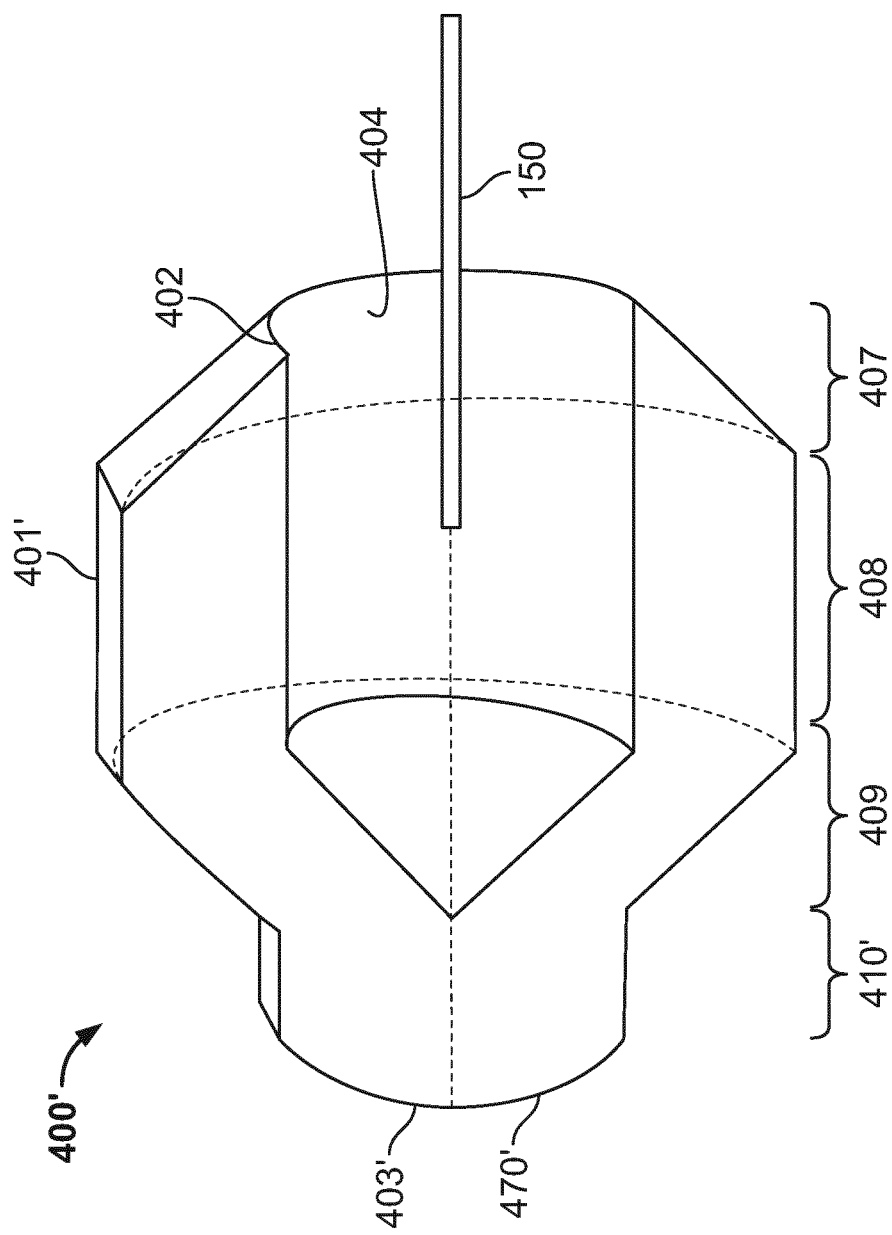
FIG. 11 is a cross-sectional view of another example optical monoblock reflector having a convex-shaped end.

In certain implementations, a lens 470 may be positioned between the second end 403 of the monoblock body 401 and the sensor 440. In the example shown, the lens 470 is a biconvex lens. In other implementations, however, any type of lens suitable for directing the light towards the sensor 440 may be utilized. In certain implementations, the lens 470 aids in focusing the image formed by the light. In certain implementations, the lens 470 may be incorporated into the monoblock reflector. For example, the second end 403' of the example monoblock 400' of FIG. 11 is convex-shaped.

Figure 12:
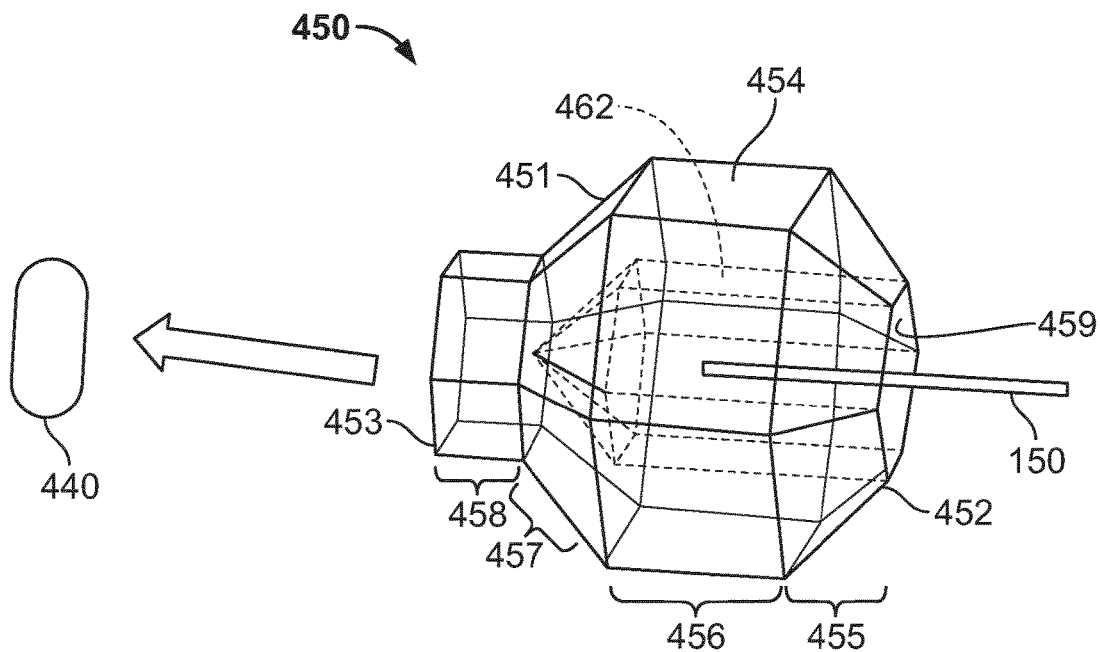
FIG. 12 is a perspective view of another example optical monoblock reflector having external flat surfaces.
Figure 13:
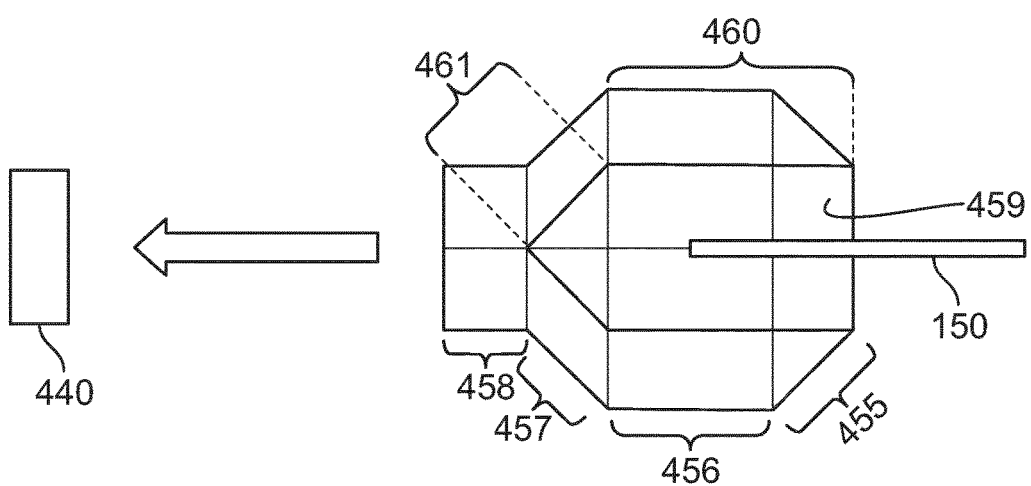
FIG. 13 is a cross-sectional view of the monoblock of FIG. 12.

In accordance with certain aspects of the disclosure, a monoblock having multiple external flat or aspheric surfaces may be utilized. FIGS. 12 and 13 illustrate an example of a reflective monoblock 450 having multiple external flat surfaces. The optical monoblock reflector 450 has a body 451 extending from a first end 452 to a second end 453. The body 451 is formed of a transparent material (e.g., glass, transparent plastic, etc.) and includes multiple reflective surfaces. The body 451 includes multiple flat external surfaces 454. In the example shown, the body 451 defines a hexagonal-shaped lateral cross-section. In other implementations, however, the body 451 may define a triangular-shaped cross-section, a rectangular-shaped cross-section, or any other planar shape.

The planar surfaces 454 of the body 451 taper outwardly from the first end 452 of the body 451 towards the second end 453 to form a first section 455 of the body 451. The body 451 has a generally constant width across a second section 456 of the body 451. The planar surfaces 454 of the body 451 taper inwardly from the second section 456 towards the second end 453 of the body 451 to form the third section 457 of the body 451. The body 451 also has a generally constant width across a fourth section 458 of the body 451 from the third section 457 to the second end 453 of the body 451.

The body 451 defines an axial passage 459 extending partially through the body 451 from the first end 452. The passage 459 includes a first faceted section 460 that extends inwardly from the first end 452 of the body 451 to a second faceted section 461. Portions of the facets 462 of the first faceted section 460 extend generally parallel to the flat external facets 454 of the second external section 456. In the example shown, the facets 462 of the first section 460 form a generally hexagonal shape. Facets 462 of the second faceted section 461 extend generally parallel to the flat external facets 454 of the third external section 457. Accordingly, the facets 462 of the second faceted section 461 tapers inwardly towards the second end 453 of the body 451 (see FIG. 13).

Figure 14:
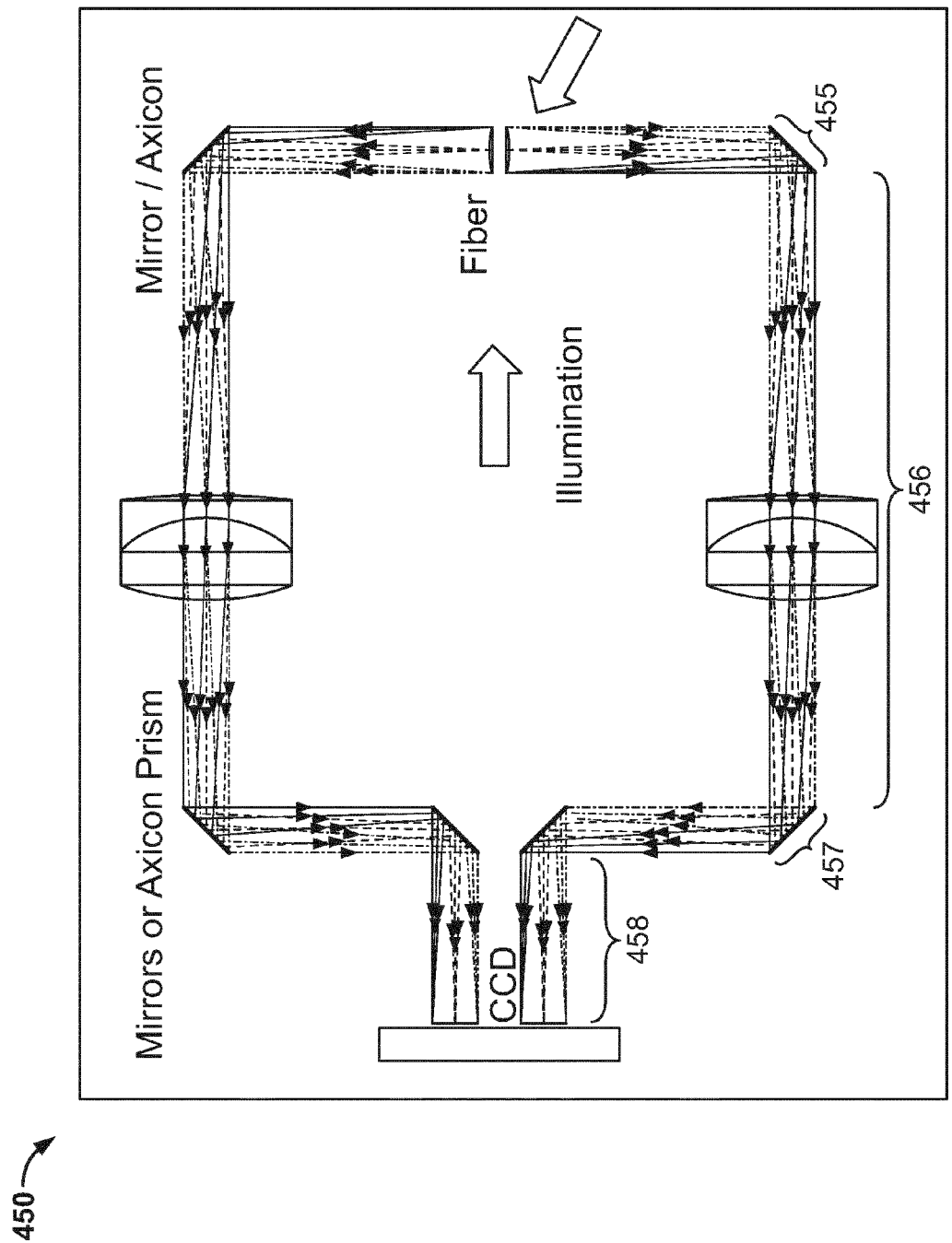
FIG. 14 is a schematic diagram illustrating how light reflects off the optical fiber and into the monoblock body of FIG. 12 when an optical fiber is positioned within the passage of the monoblock body.

When an optical fiber 150 is inserted into the passage 459 from the first end 452 of the body 451, light reflects off the fiber 150 and into the monoblock body 451 as shown schematically in FIG. 14. The light is received at an interior of the first section 455 of the body 451 and reflects off the tapered walls towards the second end 453 of the body 451. The light reflects off the tapered walls of the third section 457 of the body 451 and towards the tapered walls of the conical passage section 461. The conical passage section 461 directs the light through the fourth section 458 of the body 451 and out of the monoblock 450. In some implementations, the light reflects off the tapered surfaces due to Fresnel reflection or (total) internal reflection. In other implementations, a reflective coating may be applied to the tapered surfaces. The flat external surfaces 454 of the monoblock 450 are combined to produce a number of optic paths through the body 451. For example, axially aligned external surfaces 454 each form a separate optical path. Each optic path transmits an image of the fiber 150 to the sensor/camera from a different angle. In the example shown, the monoblock body 451 forms six optical paths that each produce an image of the optical fiber 150. Each image is rotated about 60° compared to the images obtained from adjacent paths. In other implementations, however, monoblocks may form any desired number of optical paths.

In certain implementations, a lens (e.g., lens 470 of FIG. 10) may be positioned between the second end 453 of the monoblock body 451 and the sensor 440 (FIG. 10). For example, the lens may be a biconvex lens. In other implementations, however, any type of lens suitable for directing the light towards the sensor 440 may be utilized. In certain implementations, the lens aids in focusing the image formed by the light. In certain implementations, the lens may be incorporated into the monoblock reflector 450. For example, the second end 453 of the example monoblock 450' may define a convex-shape. A convex-shaped second end 453 may aid in focusing the image as the light moves towards the sensor 440.

In some implementations, a patterned surface (e.g., patterned surface 125 of FIG. 2) may be disposed on one or more of the internal facets defining the passage 459. When the patterns are provided on facets facing non-patterned facets, the images of the fiber 150 obtained from the non-patterned facets include the visible pattern shown through the lensing effect of the fiber as described above. For example, in the hex-shaped monoblock 450 of FIG. 12, such a pattern may be provided on three of the internal facets. The other three facets receive the reflected light of the fiber and produce images of the fiber 150 that are each rotated 120° with respect to the other two images.

Figure 15:
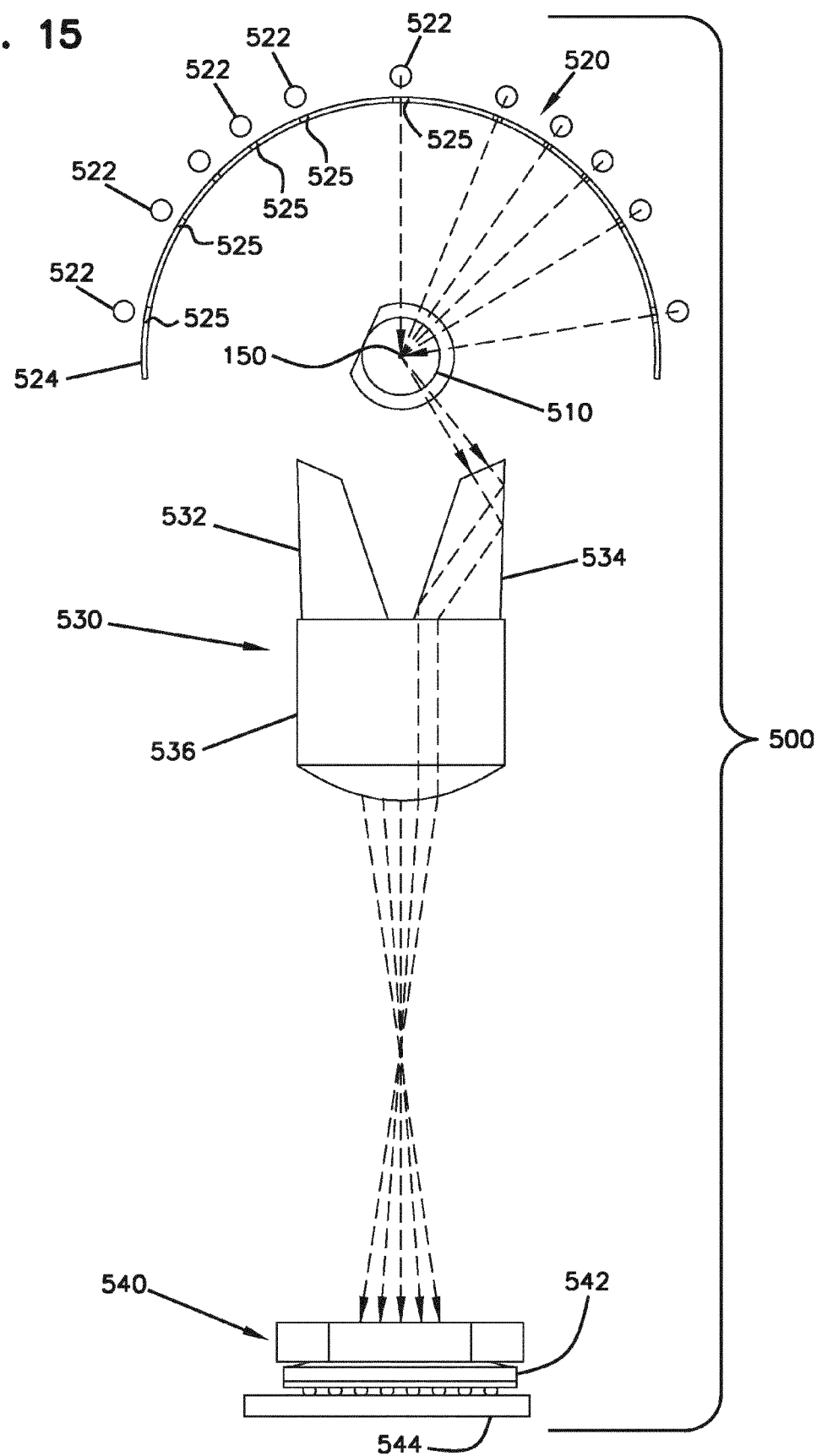
FIG. 15 is a schematic diagram of a visual inspection system including an axial illumination source, a pattern source, a lens arrangement, and a camera in accordance with aspects of the disclosure.

FIG. 15 is a schematic diagram showing a visual inspection system 500 by which optical fibers 150 may be inspected for contamination and/or damage. The example visual inspection system 500 includes an axial illumination source 510, a pattern source 520, an optical lens arrangement (e.g., focusing lens) 530, and a camera arrangement (e.g., light sensor) 540. The visual inspection system 500 is configured to hold the optical fiber 150 to align a longitudinal axis of the optical fiber 150 with the axial illumination source 510 so that light emitted from the axial illumination source 510 shines down the longitudinal axis of the optical fiber 150.

The visual inspection system 500 also holds the optical fiber 150 relative to the pattern source 520 so that a pattern formed by the pattern source 520 is visible through the optical fiber 150 at the camera 540.

In some implementations, the pattern source 520 projects a pattern radially towards the annular sidewall of the optical fiber 150. In certain implementations, the pattern source 520 projects the pattern using multiple beams of light radially directed towards the fiber 150. In the example shown, multiple radial illumination sources (e.g., LEDs) 522 are disposed at least partially around the annular sidewall of the optical fiber 150. A shield 524 is disposed between the radial illumination sources 522 and the fiber 150. Slots 525 defined in the shield 524 enable slits (e.g., rectangles or other shapes) of light to travel towards the annular sidewall of the optical fiber 150. For ease in viewing, these light rays are only depicted on the right side of FIG. 15. The combination of the light slits forms a striped pattern along the fiber 150. In still other implementations, a partially transparent screen may be disposed in one or more slots 525 to define a pattern when the light shines through the slots 525.

In some implementations, each radial illumination source 522 is associated with a single slot 525. In other implementations, each radial illumination source 522 is associated with multiple slots 525. In still other implementations, multiple radial illumination sources 522 are associated with a single slot 525. In some implementations, the radial illumination sources 522 are evenly circumferentially spaced about the optical fiber 150. In other implementations, the radial illumination sources 522 are spaced at varying circumferential distances from each other. In some implementations, the radial illumination sources 522 extend less than 270° around the optical fiber 150. In certain implementations, the radial illumination sources 522 extend less than 220° around the optical fiber 150. In certain implementations, the radial illumination sources 522 extend no more than 180° around the optical fiber 150.

The lens arrangement 530 is positioned between the optical fiber 150 and the camera 540. The lens arrangement 530 is configured to focus the light received from the optical fiber 150 onto the camera 540. In some implementations, the lens arrangement 530 includes one or more prisms 532, 534 coupled (e.g., glued) to a focusing lens 536. In other implementations, the lens arrangement 530 includes an monolithically-formed mono-block (e.g., of optical plastic) including prism portions 532, 534 and a focusing lens portion 536. In the example shown, the focusing lens portion 536 receives light rays directly from the optical fiber 150 and receives light rays passing through the prisms 532, 534. The prism portions 532, 534 receive light rays originally traveling from the optical fiber 150 in directions away from the focusing lens portion 536 and redirect the light rays towards the focusing lens portion 536.

The camera arrangement 540 is positioned to receive the focused light from the lens arrangement 530. In some implementations, the camera arrangement 540 includes a light sensor (e.g., a CMOS sensor, a CCD sensor, etc.) 542 coupled to a circuit board 544. In other implementations, the camera arrangement 540 includes a still-photograph camera that is configured to obtain one or more still images of the optical fiber 150. In still other implementations, the camera arrangement 540 includes a video camera that is configured to obtain a continuous sequence of images over a duration of time.

A method for visually inspecting optical fibers 150 using the visual inspection system 500 of FIG. 15 includes positioning an optical fiber 150 so that a longitudinal axis of the fiber 150 aligns with the axial illumination source 510 and so that the radial illumination sources 522 face towards the annular sidewall of the fiber 150. In certain implementations, the fiber 150 is positioned so that the lens arrangement 530 is configured to receive light from a portion of the fiber 150 adjacent to and including the tip of the optical fiber 150. For example, the fiber 150 can be positioned so that the lens arrangement 530 is configured to receive light from a portion along the length of the fiber 150 extending from the tip no more than five millimeters. In an example, the portion extends along the length of the fiber 150 from the tip no more than three millimeters. In an example, the portion extends along the length of the fiber 150 from the tip about two millimeters.

The axial illumination source 510 is activated to shine light into the tip of the optical fiber 150, thereby illuminating at least the portion of the length of the optical fiber 150. The camera 540 is activated to obtain an image from the light that traveled from the illuminated portion of the optical fiber 150, through the lens arrangement 530, to the camera 540. The axial illumination source 510 is deactivated after the image is obtained.

The radial illumination sources 522 are activated to shine light through the slots 524 in the shield and onto the sidewall of the optical fiber 150 to form a striped pattern or other pattern. The camera 540 is activated to obtain an image from the light that traveled from the patterned portion of the optical fiber 150, through the lens arrangement 530, to the camera 540. The radial illumination sources 522 are deactivated after the image is obtained.

The visual inspection method also can include analyzing the images obtained of the fiber 150 under axial illumination and/or radial illumination. For example, the images can be analyzed by a computer processor using an analysis algorithm and/or can be analyzed manually by a person viewing the images on a screen or other display. The images are analyzed to determine a distortion level of the pattern, the amount of debris on the fiber 150, and whether any damage (e.g., chips, splits, cracks, etc.) is visible.

Figure 16:
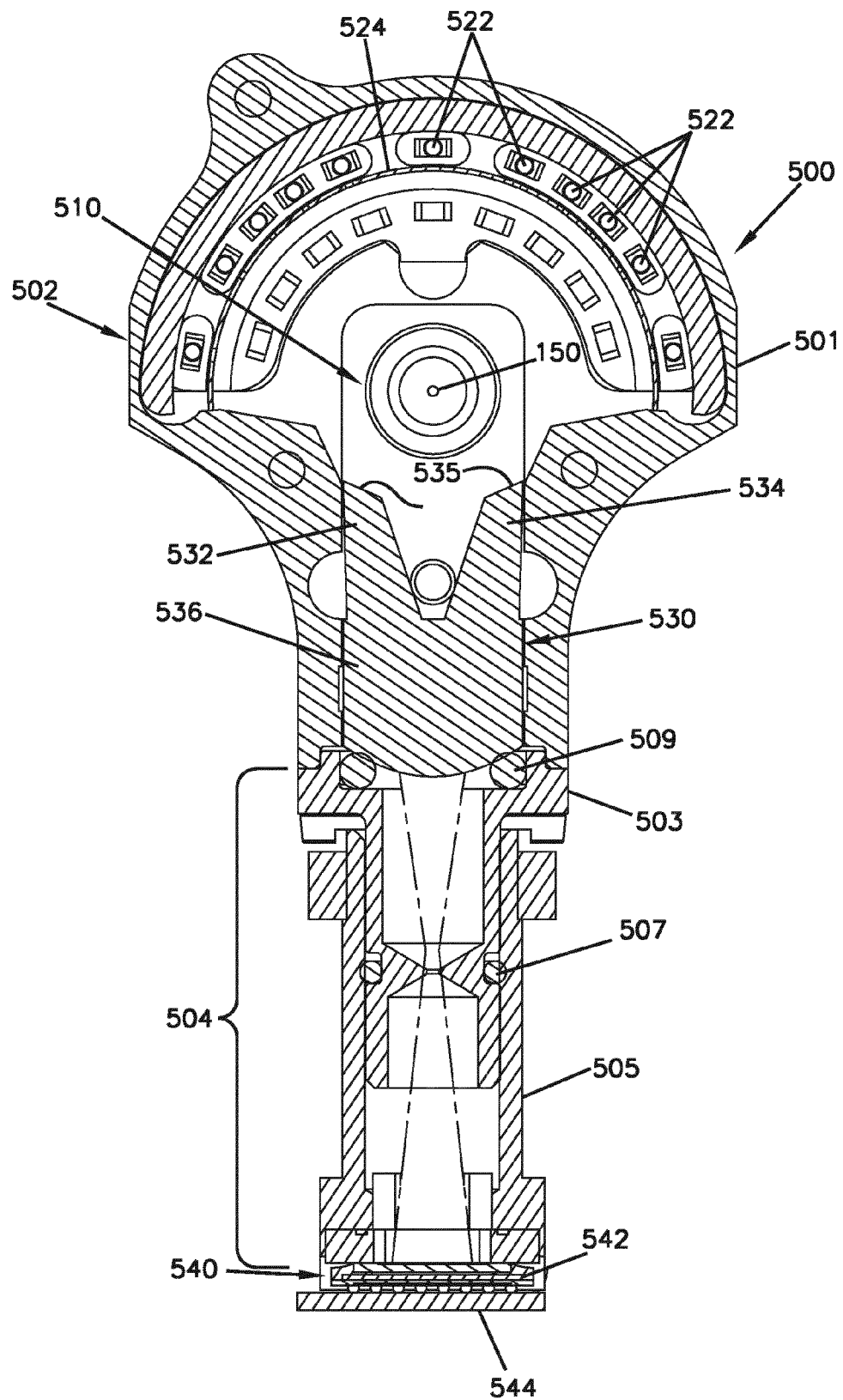
FIG. 16 is a transverse cross-sectional view of a tool implementing the visual inspection system shown in FIG. 15.
Figure 17:
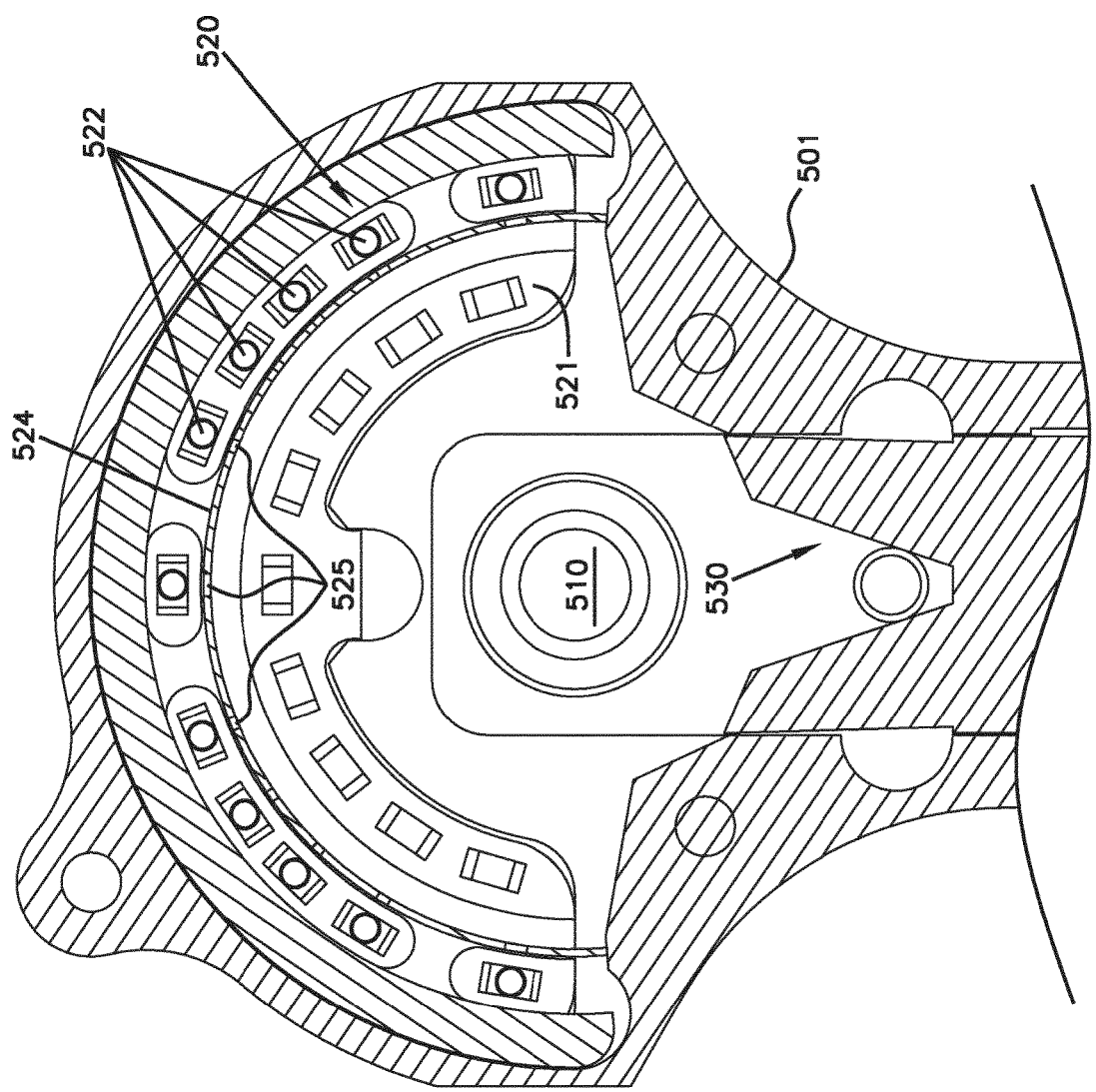
FIG. 17 is an enlarged view of a portion of FIG. 16.
Figure 18:
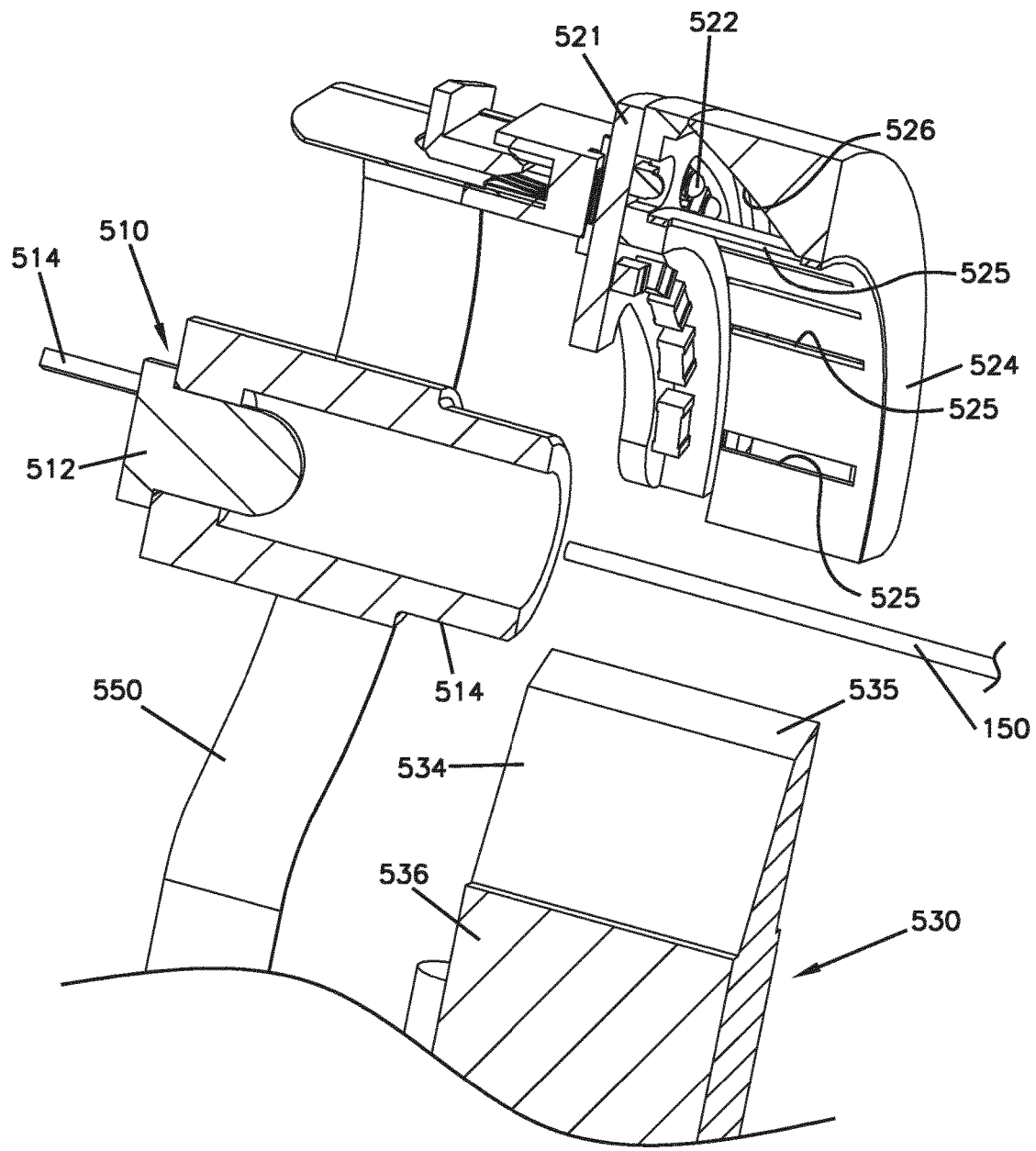
FIG. 18 is a perspective view of a cross-section taken through select portions of the tool of FIG. 16 so that the axial illumination source, part of the pattern source, and part of the lens arrangement are visible.

FIGS. 16-18 illustrate one example tool 502 that can be used to implement the visual inspection system 500. The tool 502 includes one or more housing pieces that are configured to hold the visual inspection components 510, 520, 530, and 540. The tool 502 includes a first housing portion 501 that is configured to hold the axial illumination source 510, the pattern sources 520, and the focusing lens arrangement 530. In an example, the axial illumination source 510 includes a connection pin 514 or other connector that connects to a cable, circuit board, processor, or other control circuit to activate/deactivate the axial illumination source 510. The first housing portion 501 also defines an opening through which the optical fiber 150 can enter the tool 502. The first housing portion 501 holds the axial illumination source 510 in line with the fiber opening. In certain implementations, the fiber 150 is held in a rotationally fixed position within the tool 502.

The first housing portion 501 holds a circuit board 521 on which the radial illumination sources (e.g., LEDs) 522 are mounted. In certain implementations, the circuit board 521 curves in a half-circle or half-ring shape. The shield 524 extends outwardly from the circuit board 521. Slots 525 in the shield 524 extend outwardly from the LEDs 522. The shield 524 can define angled surfaces 526 that direct light from the LEDs 522 through the slots 525. For example, the angle surfaces 526 can partially face the LEDs 522 and partially face the slots 525 (see FIG. 18). A flexible cable 550 or other communications media can connect to the circuit board 521 to control activation of the LEDs 522.

The first housing portion 501 is configured to position the optical fiber 150 between the LEDs 522 and the lens arrangement 530. In certain implementations, the first housing portion 501 positions the lens arrangement 530 so that the prisms 532, 534 are disposed at opposite sides of the fiber 150. Receiving surfaces 535 of the prisms 532, 534 are angled to face towards the optical fiber 150. In certain implementations, the focusing lens portion 536 of the lens arrangement 530 is positioned between the fiber 150 and the camera 540 so that some light rays from the fiber 150 enter the focusing lens portion 536 without passing through the prisms 532, 534 first.

The first housing portion 501 is coupled to a camera housing 504 (e.g., at a gasketed end of the camera housing 504) through which the light travels from the lens arrangement 530 to the camera 540. The camera housing 504 is sized so that the light from the lens arrangement 530 is properly focused when it reaches the camera 540. In some implementations, a length of the camera housing 504 is adjustable. For example, the camera housing 504 can be formed from second and third housing portions 503, 505 that fit together in a telescoping manner. A first gasket 507 is disposed between the second and third housing portions 503, 505 to inhibit dust or other contaminants from reaching the camera 540 from an exterior of the tool 502. A second gasket 509 is provided at the gasketed end of the camera housing 504 to facilitate seating the lens arrangement 530 in line with the camera 540.

The above specification, examples and data provide a complete description of the manufacture and use of the composition of the invention. Since many embodiments of the invention can be made without departing from the spirit and scope of the invention, the invention resides in the claims hereinafter appended.

PARTS LIST 100 visual inspection system
110 securement location 115 fiber securement arrangement
116 base
118 clamp
120 first screen
125 patterned surface
130 first radial illumination source
140 first camera
145 camera lens
150 optical fiber
155 visible pattern
160 axial illumination source
170 first image
180 second image
190 third image
AL longitudinal axis
A1 radial illumination axis
A2 axial illumination axis
200 visual inspection system
210 securement location
215 fiber securement arrangement
216 base
220A first screen
220B second screen
220C third screen
230A first radial illumination source
230B second radial illumination source
230C third radial illumination source
240A first camera
240B second camera
240C third camera
260 axial illumination source
300 computer
301 processor
302 ROM
303 BIOS
304 RAM
305 operating system
306 optical drive
307 stored images
308 hard drive
309 scoring software
310 camera interface
311 systems bus
312 display interface port
314 display device
316 IO interface port
318 input device
320 network interface port
322 local network
324 Internet
800 inspection process
802 start module
804 obtain operation
806 inspection operation
808 scoring operation
810 stop module
400 optical monoblock reflector
401 body
402 first end
403 second end
404 passage
405 cylindrical section
406 conical section
407 first section of body
408 second section of body
409 third section of body
410 fourth section of body 440 sensor
470 lens
400' optical monoblock reflector
401' body
403' second end
470 convex-shaped end
450 optical monoblock reflector
451 body
452 first end
453 second end
454 flat external surface
455 first section of body
456 second section of body
457 third section of body
458 fourth section of body
459 passage
460 first faceted section
461 second faceted section
462 facets
500 visual inspection system
501 first housing portion
502 tool
503 second housing portion
504 camera housing
505 third housing portion
507 first gasket
509 second gasket
510 axial illumination source
514 connection pin
520 pattern source
521 circuit board
522 radial illumination sources
524 shield
525 slots
526 angled surfaces
530 optical lens arrangement
532, 534 prism
536 focusing lens portion
540 camera arrangement
542 camera/light sensor
544 circuit board
550 flexible cable

The invention claimed is:

1. A method for visually inspecting optical fibers comprising:
positioning an optical fiber so that light shines from a radial light source through a slotted shield towards the optical fiber to produce a pattern visible through the optical fiber when viewed through an annular side of the optical fiber, wherein positioning the optical fiber comprises positioning the optical fiber a sufficient distance from the shield so that the pattern is visible only through the optical fiber in the image;
positioning an imaging sensor so that the optical fiber is disposed between the imaging sensor and the slotted shield;
shining light from the radial light source through the slotted shield, through the annular side of the optical fiber and towards the imaging sensor;
obtaining at least one image of at least a portion of the annular side of the optical fiber using the imaging sensor, the pattern being at least partially visible through the annular side of the optical fiber in the at least one image;
analyzing the pattern in the image to detect distortions in the pattern;

shining an axial illumination source along a longitudinal axis of the optical fiber;

obtaining at least a second image of at least a portion of the optical fiber using the imaging sensor while the axial illumination source is shining towards the optical fiber; and analyzing the second image to detect contamination on the optical fiber.

2. The method of claim 1, wherein positioning the optical fiber comprises positioning the optical fiber at a distance ranging from about 6 mm to about 20 mm from the shield.

3. The method of claim 1, wherein positioning the imaging sensor so that the optical fiber is disposed between the imaging sensor and the slotted shield comprises positioning the imaging sensor so that the camera lens is between about 10 mm and about 40 mm away from the optical fiber.

4. The method of claim 3, wherein the imaging sensor includes a camera having a camera lens, and wherein positioning the imaging sensor so that the optical fiber is disposed between the imaging sensor and the slotted shield comprises positioning the camera so that the camera lens is about 20mm from the optical fiber.

5. The method of claim 1, wherein the imaging sensor includes a photographic camera.

6. The method of claim 1, wherein the imaging sensor includes a video camera.

7. The method of claim 1, further comprising, processing the at least one image using vision analysis and scoring software to produce a quantitative evaluation of an amount of contamination on the optical fiber.

8. The method of claim 1, wherein the imaging sensor comprises a camera having a camera lens.

9. A visual inspection system by which optical fibers are inspected for contamination or damage, the visual inspection system comprising:

a securement arrangement configured to retain an optical fiber;

a shield defining a plurality of slots;

a radial illumination source configured to shine light through the slots of the shield towards the securement arrangement, the light shining through the slots producing a pattern at the securement arrangement;

an axial illumination source configured to shine light along a longitudinal axis of the optical fiber;

at least a first imaging sensor positioned at an opposite side of the securement arrangement from the slotted shield, the first imaging sensor being configured to obtain at least a first image of a circumferential side of any optical fiber held at the securement arrangement when the radial illumination source is shining, the pattern produced by the light shining through the slots being visible through the optical fiber in the at least one image, wherein the securement arrangement retains the optical fiber at a sufficient distance from the shield so that the pattern is visible only through the optical fiber in the image, the first imaging sensor also being configured to obtain at least a second image of at least a portion of the optical fiber while the axial illumination source is shining.

10. The visual inspection system of claim 9, wherein the first imaging sensor includes a video camera.

11. The visual inspection system of claim 9, wherein the first imaging sensor includes a photographic camera.

12. The visual inspection system of claim 9, wherein the radial illumination source includes at least one LED.

13. The visual inspection system of claim 9, further comprising an axial illumination source configured to direct light along a longitudinal axis of any optical fiber held at the securement arrangement.

14. The visual inspection system of claim 12, wherein the radial illumination source includes a plurality of LEDs.

15. The visual inspection system of claim 14, wherein each LED aligns with one of the slots defined in the shield.

16. The visual inspection system of claim 15, wherein the LEDs face in a different direction than the slots.

17. The visual inspection system of claim 9, further comprising a lens arrangement disposed between the securement arrangement and the first imaging sensor.

18. The visual inspection system of claim 17, wherein the lens arrangement includes a focusing lens configured to focus light passing through the optical fiber onto the first imaging sensor.

* * * * *